United States Patent
Gourvest et al.

Patent Number: 5,202,314
Date of Patent: Apr. 13, 1993

[54] 10-THIOETHYL-STEROIDS

[75] Inventors: Jean-Francois Gourvest, Joinville Le Pont; Dominique Lesuisse, Paris, both of France

[73] Assignee: Roussel Uclaf, Romainville, France

[21] Appl. No.: 886,977

[22] Filed: May 21, 1992

[30] Foreign Application Priority Data

May 27, 1991 [FR] France ............... 91 06332

[51] Int. Cl.$^5$ ............... A61K 31/58; C07J 1/00
[52] U.S. Cl. ............... 514/172; 514/177; 514/179; 540/87; 552/615
[58] Field of Search ............... 540/87; 552/615; 514/172, 177, 179

[56] References Cited

U.S. PATENT DOCUMENTS 4,925,834  5/1990  Bohlmann et al. ............... 552/615
5,086,047  2/1992  Gourvest et al. ............... 552/610

Primary Examiner—Marianne M. Cintins
Assistant Examiner—Kimberly J. Kestler
Attorney, Agent, or Firm—Bierman and Muserlian

[57] ABSTRACT

A compound of the formula

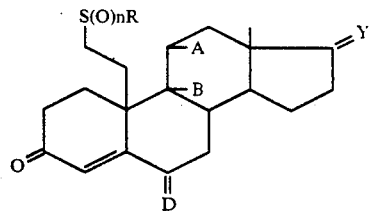

wherein R is selected from the group consisting of alkyl, alkenyl and alkynyl of up to 4 carbon atoms, Y is =O or

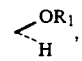

$R_1$ is hydrogen or acyl, n is 0, 1 or 2, D is =O or

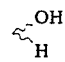

and A and B form a second carbon-carbon or an α-epoxy useful for aromatase inhibition and a process and intermediates for their preparation.

7 Claims, No Drawings

10-THIOETHYL-STEROIDS

OBJECTS OF THE INVENTION

It is an object of the invention to provide the novel steroids of formula I and a novel process and novel intermediates therefore.

It is another object of the invention to provide novel aromatase inhibiting compositions and a novel method of inducing aromatase inhibiting activity in warm-blooded animals.

These and other objects and advantages of the invention will become obvious from the following detailed description.

THE INVENTION

The novel compounds of the invention have the formula

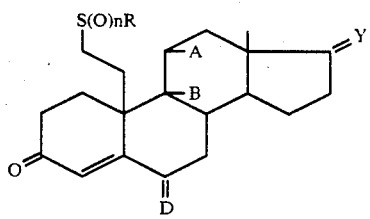

wherein R is selected from the group consisting of alkyl, alkenyl and alkynyl of up to 4 carbon atoms, Y is =O or $$\overset{OR_1}{\underset{H}{\diagdown}}$$

$R_1$ is hydrogen or acyl, n is 0, 1 or 2, D is =O or

and A and B form a second carbon-carbon bond or an α-epoxy.

Among the preferred alkyl are methyl, ethyl, propyl, isopropyl, butyl, isobutyl, secondary butyl, tert-butyl. Examples of suitable alkenyl and alkynyl are vinyl, allyl, 1-propenyl, ethynyl, 1- or 2-propynyl.

Among the acyl of a saturated or unsaturated aliphatic or cycloaliphatic carboxylic acid are alkanoic acid such as acetic acid, propionic acid, butyric acid or isobutyric acid, valeric acid or undecylic acid, hydroxyalkanoic acids such as hydroxyacetic acid, cycloalkylcarboxylic acid or (cycloalkyl) alkanoic acids such as cyclopropylcarboxylic acid, cyclopentylcarboxylic acid or cyclohexylcarboxylic acid, cyclopentyl acetic acid or propionic or cyclohexyl acetic or propionic acid, benzoic acid or phenylalkanoic acid such as phenylacetic or phenylpropionic acid, an amino acid such as diethylaminoacetic acid or aspartic acid or formic acid. The acetyl, propionyl or benzoyl are preferred.

Among the values of R, methyl or ethyl are preferred and among the values of $R_1$, hydrogen or acetyl are preferred.

More particularly, a preferred group of compounds of the invention are those of the formula

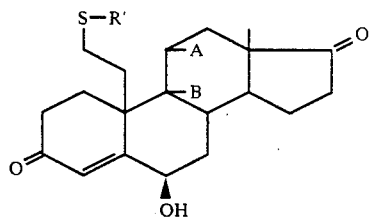

in which A and B have the above meaning and R' is alkyl of 1 to 4 carbon atoms.

Among the preferred products of formula I' are those wherein R' is methyl or ethyl, particularly methyl. Specific products of formula I' are 10 β-[2-methylthio-ethyl]-Δ4,9(11)-estradiene-6 β-ol-3-17-dione, 9α, 9 α, 11α, -epoxy-10β-[2-methylthio-ethyl]-Δ4-estrene-6β-ol-3,17-dione.

The novel process of the invention for the preparation of the compounds of formula I comprises reacting a product of the formula

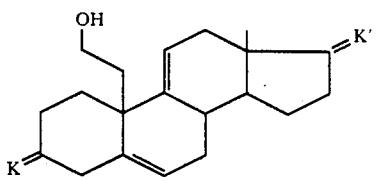

in which K and K' individually are protected keto with an epoxidation reagent to obtain the products of the formula

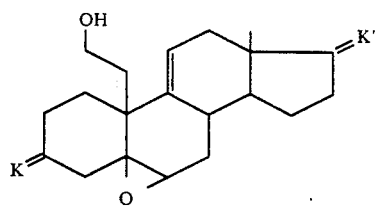

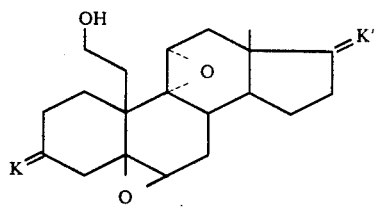

reacting the latter either with a conversion reagent of hydroxy into thiol to obtain the products of the formulae

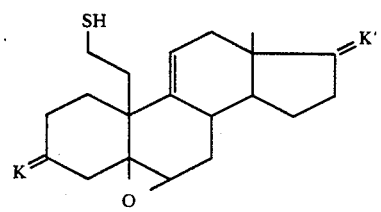

reacting the latter with a reactive derivative of R to obtain the products of the formulae

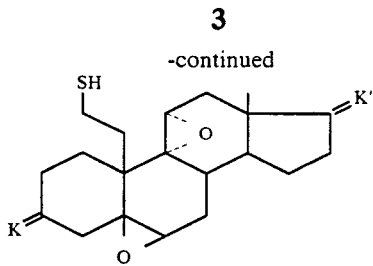

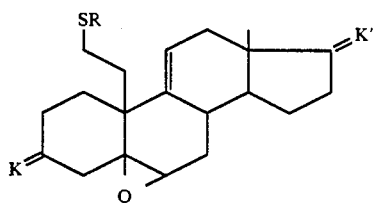

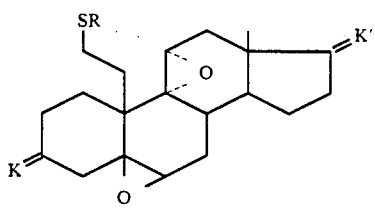

or with a reactive derivative of a sulfonic acid to obtain the products of the formulae

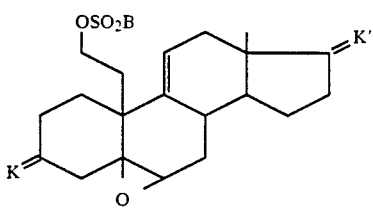

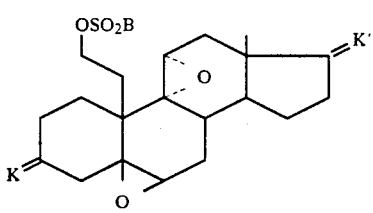

wherein B is the remainder of a sulfonic acid, reacting the latter with a salt of the formula RSA wherein A is a monovalent cation to obtain products of formulae Va and Vb as defined above, which are treated with a deprotection reagent of the protected ketone and opening of the 5(6) epoxide to obtain products of the formulae

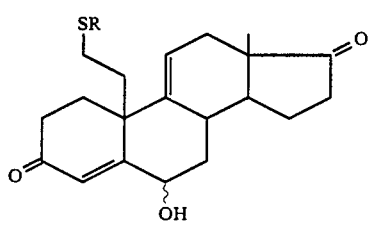

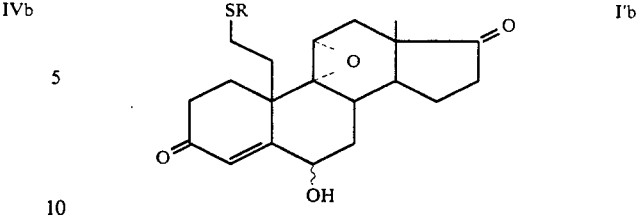

corresponding to products of formula I in which R has the above meaning, Y is oxygen, n is 0, and D is

which products of formula I′a and I′b are optionally subjected to any one of the following reactions:
 (a) reduction optionally followed by an acylation of the 17-ketone,
 (b) oxidation of the sulfur atom of —SR into sulfoxide or sulfone,
 (c) oxidation of 6-hydroxyl to the ketone.

In the preferred operating conditions of the process, the epoxidation reagent is 3-chloroperbenzoic acid or its magnesium salt or also hydrogen peroxide in the presence of hexachloro (or hexafloro) acetone, or also potassium peroxymonosulfate (oxone) and the conversion reagent of hydroxyl into thiol is diethyl axoidcarboxylate in the presence of triphenylphosphine and thioacetic acid. In this way, a product containing a 10β-acetyl-thioethyl is obtained intermediately, which is converted into a thiol by the action of hydrazine. The two stages of the reaction are preferably carried out in an aprotic solvent such as tetrahydrofuran or diethyl ether.

The reactive derivative of R which is preferably used is a halide such as chloride or bromide, but a pseudohalide such as mesylate or tosylate can also be used. The reaction takes place in the presence of a strong base such as an alkali metal alcoholate such as potassium tert-butylate or an amide such as diisopropyl lithium amide, or lithium or potassium hexamethyldisilylazanate. The operation can be carried out in a solvent such as tetrahydrofuran at low temperatures between 0° and −78° C. The reactive derivative of the sulfonic acid of formula BSO₃H in which B is methyl or tolyl is preferably a halide such as chloride and mesyl chloride is preferably used. The reaction preferably takes place in the presence of a mineral or organic base, preferably triethylamine and a reaction solvent such as methylene chloride is sued at a temperature on the order 0° C.

The salt of formula RSA in which R has the previous meaning is preferably a salt of an alkali metal such as sodium or lithium. The action of this salt is preferbly carried out in an aprotic solvent such as tetrahydrofuran, hexamethylphosphoramide or dimethylformamide and the reaction can take place in the presence of a crown ether specific to the metal used such as 12-crown-4 for lithium, 15-crown-5 for sodium, or 18-crown-6 for potassium. The action of the salt of formula RSA on the products of formulae VIa and VIb can lead to a total or partial deblocking of one or two of the protected 3- and 17- ketone functions.

In the particular, the products of formulae V′a and V′b can be obtained:

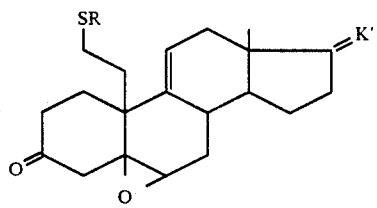

V'a

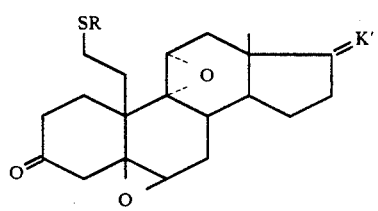

V'b which can lead to products of formulae I'a and I'b under the same conditions as the products of formulae Va and Vb. The hydrolysis of the products of formulae V'a and V'b into products of formulae I'a and I'b is preferably an acid hydrolysis using dilute hydrochloric acid (2 to 6N) or acetic acid in a solvent such as ethanol or tetrahydrofuran.

The reduction of the 17-ketone is carried out using a hydride such as sodium borohydride in a solvent such as methanol and the optional acylation of the 17-ketone function is carried out by the action of the reactive derivative of the acyl to be introduced. Thus, an acid halide can be used, particularly an acid chloride or a mixed or symmetrical anhydride. For example, acetyl chloride or acetic anhydride can be mentioned. The optional oxidation of the sulfur atom into sulfoxide is carried out by the action of a periodate such as sodium periodate in an aqueous solvent such as aqueous methanol or a peracid such as metachloroperbenzoic acid in a solvent such as dichloromethane. The optional oxidation of the sulfur into a sulfone is carried out using a peracid such as metachloroperbenzoic acid. The oxidation of the 6-hydroxyl into the ketone is carried out using oxalyl dimethyl sulfoxide chloride (Swern's reagent) or, aluminum triisopropoxide in the presence of cyclohexanone.

The protected ketos represented by K and K' are preferably chosen from the cyclic or non-cyclic diethers such as ethylenedioxy, dimethylpropylenedioxy, dimethoxy or diethoxy.

In a modification of the process of the invention, the compounds of formula Va and Vb are reacted under carefully controlled conditions to obtain the compounds of the formulae

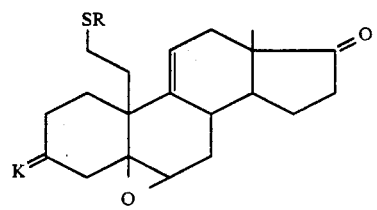

VIIa

-continued

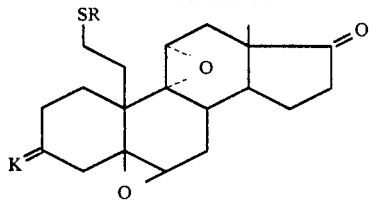

VIIb reacting the latter with a deprotection reagent of the ketone and opening of the 5(6) epoxide to obtain the products of formulae I'a and I'b as defined above.

The carefully-controlled conditions under which the conversion of the products of formulae Va and Vb into the products of formulae VIIa and VIIb is carried out consisting of using hydrochloric acid which is more dilute than that indicated above for example, normal hydrochloric acid in a solvent such as ethanol. The subsequent conversion of the products of formulae VIIa and VIIb into products of formulae I'a and I'b is carried out under the same conditions using normal hydrochloric acid in ethanol.

The observation that approximately 35% of breast cancers are estrogeno-dependent has led to the research of ways to limit the production of estrogen. After having used surgical methods consisting of suppressing the estrogen sources (ovaries) or the sources of their biosynthetic precursors, the androgens (suprarenal glands), the development of less traumatic methods was sought. (ABUL-HAJJ Steroid Biochem. Vol. 13, (1980), p. 1935; BRODIE Cancer Res., Vol. 42, (1982), page 3312).

In this regard, the specific inhibition of the last enzymatic stage of the aromatization of 3-keto Δ-4 androgens into phenolic estrogens appears to be the most effective and least disturbing way. The enzyme responsible for this conversion is a monooxygenase known as P450 cytochrome: AROMATASE (BRODIE J. Endocrinol. Invest. Vol. 2, (1979), p. 445) which requires oxygen and NADPH (reduced Nicotinamide Adenine Dinucleotide phosphate) to carry out the aromatization of the androgens into estrogens.

Based on another mechanism, other authors (for example MARCOTTE et. al., Biochemistry, Vol. 21, (1982), p. 2773, FLYNN et. al. Biochem. Biophys. Res. Com. Vol. 103, (1981), p. 713) have proposed suicide inhibitors for Aromatase. Competitive inhibitors such as Aminoglutethimide have also been proposed for the treatment of metastasic cancers of the breast. This product however has proved not to be specific to Aromatase. Indeed, it attacks enzymatic processes other than that leading from androgens to estrogens.

The novel aromatase inhibiting compositions of the invention are an aromatase inhibiting effective amount of at least one compound of formula I and an inert pharmaceutical carrier. The compositions may be in the form of tablets, dragees, capsules, granules, suppositories, pessaries ointments, creams, gels, patches and injectable preparations.

Examples of suitable excipients or carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions of the invention have a specific aromatase activity (cytochrome P450 aromatase) and this aromatase inhibiting property makes the compositions useful in hormono-dependent pathologies, such as estrogeno-dependent, cancers of the breast, endometrium, ovary and pancreas, gynecomastia, begnign disorders of the breast, endometriosis, polycystic diseases of the ovary, prostatic hyperplasia and more generally in the treatment of hyperestrogenemias and certain forms of obesity.

The novel method of inducing aromatase inhibiting activity in warm-blooded animals, including humans, comprises administering to warm-blooded animals an aromatase inhibiting effective amount of at least one compound of formula I. The compounds may be administered orally, rectally, parenterally or locally by the transdermal route. The usual effective dose is 0.1 to 50 mg/kg depending upon the condition treated, the method of administration and the specific compounds.

The novel intermediates of the invention are those of formulae IIIa, IIIb, IVa, IVb, Va, Vb, VIIa and VIIb.

The starting compounds of formula II can be made by a Claisen rearrangement of a compound of the formula

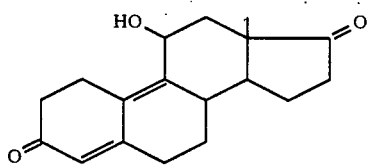

A to obtain a product of the formula

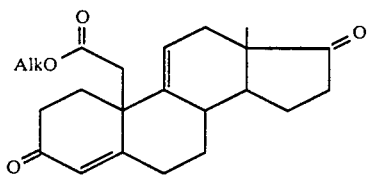

B in which Alk is alkyl of 1 to 4 carbon atoms, and reacting the latter with one or two protective reagents of the ketone to obtain a product of the formula.

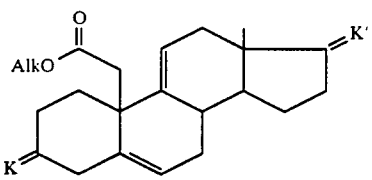

C and reducing the latter to obtain the products of formula II.

In a preferred method for implementing the Claisen rearrangement, it is carried out using an alkyl orthoacetate, preferably ethyl, in the presence of an organic acid such as propionic acid and optionally in a solvent such as xylene. The reaction is preferably carried out at high temperatures.

The protection reagent of the ketones is chosen from alcohols or diols and preferably ethylene glycol is used. The reaction is carried out in the presence of an acid such as p-toluenesulfonic acid by heating, for example at reflux of a solvent such a dichloroethane, or by using ethylene glycol as solvent. The reduction of the products of formula C is carried out using a hydride, preferably lithium aluminum hydride. The operation takes place in an aprotic solvent such as tetrahydrofuran or ethyl ether, for example at ambient temperature.

In the products of formulae B and C, Alk preferably is ethyl. The product of formula A is described in U.S. Pat. No. 3,282,785.

The expression "12-crown-4" means 1,4,7,10-tetraoxacylododecane; "15-crown-5" is 1,4,7,10,13-pentaoxacyclopentadecane and "18-crown-6" is 1,4,7,10,13,16-hexaoxacyclooctadecane.

In the following examples, there are described several preferred embodiments to illustrate the invention. However, it is to be understood that the invention is not intended to be limited to the specific embodiments.

EXAMPLE 1

$10\beta$-[2-methylthio-ethyl]-$\Delta^{4,9(11)}$-estradiene-$6\beta$-ol-3,17-dione STEP A: Ethyl $\Delta^{4,9(11)}$-androstadiene-3,17-dione-19-carboxylate A mixture of 500 mg of $\Delta^{4,9}$-androstadiene-$11\beta$-ol-3,17-dione (described in U.S. Pat. No. 3,282,785), 5 ml of triethyl orthoacetate and 6.4 mg of propionic acid was heated to a temperature of 137° C. and after heating for 4 hours, the reaction mixture was concentrated to dryness. The residue was chromatographed on silica (eluant: ethyl acetate - hexane 1—1) to obtain 503 mg of the expected product with a Rf=0.33.

NMR (CDCl$_3$, 250 MHz): 0.94 (s, 18 Me); 1.23 (t, COOCH$_2$CH$_3$) 3.94 to 4.29 (m, COOCH$_2$CH$_3$), 5.61 (m, H11), 5.84 (wide s, H$_4$).

IR (CHCl$_3$): 1732 cm$^{-1}$ (17-ketone), 1662, 1612 (conjugated ketone).

STEP B: Ethyl 3,17-bis(ethylenedioxy)-$\Delta^{5,9(11)}$-androstadiene-19-carboxylate (Product IV)

2 ml of ethylene glycol and 100 mg of p-toluene-sulfonic acid were added to a mixture of 503 mg of the product of Step A in solution in 30 ml of dichloroethane and the mixture was refluxed for 8 hours. 1 ml of triethylamine was added and the mixture was concentrated. After chromatography on silica (eluant: ethyl acetate - hexane (3-7)), 450 mg of the expected product with a Rf=0.47 (ethyl acetate - hexane (1-1)) were obtained.

STEP C: cyclic ($5\beta$, $6\beta$, $10\beta$) 3,3,17,17-bis(1,2-ethanediyl) acetal of 5(6)-epoxy-10-(2-hydroxyethyl)-$\Delta^{9(11)}$-estrene-3,17-dione (product A) and cyclic ($5\beta$, $6\beta$, $9\alpha$, $10\beta$, $11\alpha$) 3,3,17,17-bis(1,2-ethanediyl) acetal of 5(6)-$\Delta^{9,(11)}$-diepoxy-10-(2-hydroxy-ethyl) estrane-3,17-dione (product B)

2.08 g of 80% metachloroperbenzoic acid were added at 0° C. to a mixture of 4 g of the product of Step B with 800 mg of sodium acetate in 40 ml of methylene chloride and the mixture was stirred for 30 minutes at 0° C. Another 2.08 g of metachloroperbenzoic acid were added and the mixture was stirred for 30 minutes. Then, the reaction medium was hydrolyzed by adding a saturated aqueous solution of sodium bicarbonate and extraction was effected with methylene chloride. The extracts were dried with magnesium sulfate and the solution was chromatographed on silica (eluant: cyclohexane - ethyl acetate (7-3) and 1% triethylamine) to obtain 1.85 g of product A and 1.7 g of product B.

NMR Spectrum: Product A (CDCl$_3$) 250 MHz. 0.82 ppm (s) 18 methyl; 3.17 ppm (d, approx. J=3) 1H epoxide; 3.5 to 4.0 ppm CH$_2$I; 5.50 ppm (m) H$_{11}$.

NMR Spectrum: Product B (CDCl$_3$) 250 MHz 0.84 ppm (s) 18 methyl; 3.05 ppm (d, J=5) H$_{11}$; 3.16 ppm (d, J=2) H$_6$ alpha; 3.75 to 4.00 ppm the ketals and CH$_2$O.

STEP D: Cyclic (5$_{62}$,6$_{62}$,10$_{62}$)-3,3,17,17-bis(1,2-ethanediyl) acetal of 5(6)-epoxy-10-[[2-(methylsulfonyl)-oxy]-ethyl]-Δ$^{9(11)}$-estrene-3,17-dione 0.68 ml of triethylamine and 0.38 ml of methane sulfonyl chloride were added to a solution of 1.85 g of the product of Step C in 20 ml of methylene chloride and the mixture was stirred for 30 minutes at 0° C., then for 1 hour at ambient temperature. 0.31 ml of triethylamine and 0.17 ml of methanesulfonyl chloride were added and the mixture was stirred for 20 minutes. The reaction medium was hydrolyzed by adding a saturated aqueous solution of sodium bicarbonate and extraction was effected with methylene chloride. After evaporating the solvent, 2.05 g of the desired product were obtained.

NMR Spectrum (CDCl$_3$ 300 MHz) ppm: 0.83 (s) 18 CH$_3$; 2.97 (m) SO$_2$CH$_3$; 3.8 to 4.0 (m) the ketals; 4.1 to 4.6 (m) CH$_2$OSO$_2$; 5.60-5.55 (m) ethylenics; 3.06 (d, J=3 HZ) 1H epoxide.

STEP E: Cyclic (5β,6β,10β) 3,3,17,17-bis(1,2-ethanediyl) acetal of 5(6)-epoxy-[2-methylthio-ethyl]-Δ$^{9(11)}$-estrene-3,17-dione 1.6 g of sodium thiomethoxide were added to a solution of 1.9 g of the product of Step D in 25 ml of dimethylformamide, and the mixture was stirred for 1 hour at ambient temperature. The dimethylformamide was evaporated off and the residue was taken up in methylene chloride, washed, dried and evaporated to dryness. The residue was chromatographed on silica (eluant: cyclohexane ethyl acetate (8-2)) to obtain 1.4 g of the desired product.

NMR Spectrum (CDCl$_3$ : 300 MHz) ppm: 0.82 (s) 18 CH$_3$; 2.08 (s) S-CH$_3$; 3.0 (d, J=approx. 3) H epoxide; 3.8 to 4.0 (m) the ketals; 5.52 (m) H ethylenics.

STEP F: 10β-[2-methylthio-ethyl]-Δ$^{4,9(11)}$-estradiene-6α-ol-3,17-dione

A mixture of 1 g of the product of Step E, with 1 ml of methylene chloride, 10 ml of ethanol and 5 ml of a solution of 1N hydrochloric acid was stirred for 4 hours at ambient temperature and then a saturated aqueous solution of sodium bicarbonate was added. Extraction was effected with methylene chloride and the organic solution was dried and concentrated to dryness. The residue was chromatographed on silica (eluant: cyclohexane ethyl acetate (8-2)) to obtain 40.1 mg of the desired product and 601 mg of cyclic 3-(1,2-ethanediyl acetal) of 5α, 6α-epoxy-10β-[2-methylthio-ethyl]-Δ$^{9(11)}$-estrene-3,17-dione.

NMR Spectrum of the desired product: (CDCl$_3$ 300 MHz) 0.91 (s) 18 CH$_3$; 2.09 (s) S-CH$_3$; .4.47 (t) after H$_6$ equatorial exchange; 5.54 (m) H$_{11}$; 5.90 (s) H$_4$; 0.86 (s) the other CH$_3$'s.

EXAMPLE 2

9α, 11α,-epoxy-10β-[2-methylthio-ethyl]-Δ$^4$-estrene-6β-ol-3,17-dione

STEP A: Cyclic (5β, 6β, 9α, 10α, 11α) 3,3,,17,17-bis(1,2-ethanediyl) acetal of 5(6), 9(11) diepoxy-10-[[2-methylsulfonyl)-oxy]-ethyl]-estrane-3,17-dione 0.42 ml of methane sulfonyl chloride and 0.75 ml of triethylamine were added to a solution cooled to 0° C. of 1.5 g of product B obtained in Step B of Example 1 in 20 ml of methylene chloride. The mixture was stirred for 1 hour at 0° C. and hydrolysis took place by adding a saturated aqueous solution of sodium bicarbonate. Extraction was effected with methylene chloride followed by drying and evaporating to dryness to obtain 1.31 g of the desired product which was used as is for the following step.

STEP B: cyclic (5β, 6β, 9α, 19β) 3,3,17,17-bis (1,2-ethanediyl) acetal of 5(6), 9(11)-diepoxy-10-[2-methylthio-ethyl]-estrane-3,17-dione 931 mg of sodium thiomethoxide were added to a solution of 1 g of the product of Step A in 10 ml of dimethylformamide and the mixture was stirred for 2 hours. The dimethylformamide was evaporated off and the residue was taken up in methylene chloride, washed, dried and evaporated to dryness. The residue was chromatographed on silica (eluant: cyclohexane - ethyl acetate (8-2)) to obtain 9-10 mg of the desired product.

NMR Spectrum: (CDCl$_3$ 300 MHz) ppm: 0.84 (s) 18 CH$_3$; 2.14 (s) S-CH$_3$; 3.08 (d, J=5.5) βH$_{11}$; 3.13 (d, J=2) alpha H$_6$; 3.75 to 4.00 the ketals.

STEP C: 9α, 11α-epoxy-10β-[2-methylthio-ethyl]-Δ$^4$-estrene-6β-ol-3,17-dione 700 mg of the product of Step B and 15 ml of ethanol and 2 ml of 2N hydrochloric acid were stirred for 72 hours at ambient of sodium bicarbonate. Extraction was effected with methylene chloride and the extracts were dried and evaporated to dryness. The residue was chromatographed on silica (eluant: cyclohexane ethyl acetate (8-2)) to obtain 335 mg of the desired product and 98.6 mg of cyclic 3-(1,2-ethanediyl acetal) of 5β,6β, 9β, 11α-diepoxy-10β-[2-methylthio-ethyl]-estra-3,17-dione.

NMR Spectrum of the desired product: (CDCl$_3$ 300 MHz) ppm 0.99 (s) 18 CH$_3$; 2.15 (s) S-CH$_3$; 3.25 (t, 1) H$_{11}$ eq., 4.52 (t, 1) H$_6$ eq., 5.96 (t, 1) H$_4$.

Pharmacological study of the products of the invention

Inhibition dependent on the concentration (measurement of IC$_{50}$=concentration of inhibitor necessary to reduce the enzymatic activity by 50%). Human placentas were used which were washed one hour at most after birth, perfused with physiological serum (5 liters) via the umbilical vein and then deep-frozen at −40° C.

(1) Obtaining the placental microsomes

The placentas were thawed at 4° C. and then homogenized (1:3) in a phosphate buffer 10 mM, pH=7.0; containing 100 millimoles of potassium chloride (KCl), 10 millimoles of dithiothreitol (DTT), 10 millimoles of ethylenediaminetetraacetic acid (EDTA), 40 millimoles of nicotinamide and 250 millimoles of sucrose. The homogenates were then subjected to different centrifugation phases until the "9000 g" supernatant was obtained (corresponding to cytosol and to endoplasmic recticulum).

The supernatant was then subjected to an ultracentrifugation stage (90 minutes, 105,000 g) to obtain the microsomal regulus. The microsomes were then resuspended in a phosphate buffer 50 millimoles, pH=7.4, containing 100 millimoles KCl, 1 millimole EDTA, 1 millimole DTT and glycerol (10%). The microsomal suspension was then aliquoted and the fractions were deep-frozen at the temperature of liquid nitrogen. The protein concentration of the microsomal suspension was determined by the BRADFORD method BRADFORD M., Anal. Biochem., Vol. 72, (1976), p. 248).

(2) Measurement of the $IC_{50}$ of each inhibitor

The following were added in any order to 960 microliters of phosphate buffer (50 millimoles, pH=7.2), 2.5 millimoles of glucose-6-phosphate and containing 0.16 international units of glucose-6-phosphate dehyrogenase (G-6-PDH):

1. 10 microliters of inhibitor solubilized in dimethylsulfoxide (DMSO) to give final concentrations from $10^{-5}$ M to $10^{-10}$M.
2. 10 microliters of substrate which was Androstenedione 500 nM solubilized in ethanol and containing $1\beta$-$2\beta$-$^3$H-Androstenedione at a known isotopic dilution (approx. 200,000 disintegrations per minute).
3. 10 microliters of microsomal suspension equivalent to 25 micrograms of proteins per test.

The enzymatic reaction was then very rapidly initiated by the addition of 10 microliters of reduced nicotinamide adenine dinucleotide phosphate (NADPH) solubilized in water. After stirring, each test was incubated at 37° C. for 10 minutes and the reaction was then halted by the addition of 4 ml of chloroform. After vigorous stirring of the tubes, they were decanted and centrifuged at 4° C. for 10 minutes at a speed of 3,000 r.p.m. (rotations by minutes) i.e. 600 g.

After centrifugation, 100 microliters of supernatant were taken from each tube and counted in the presence of a scintillating liquid. This method was derived from the procedures described by REED et. al. (J. Biol. Chem., Vol. 251, (1976), p. 1625) and THOMPSON et. al. (J. Biol. Chem., Vol. 249, (1974), p. 5364). The enzymatic activity (aromatase) was proportional to the percentage of tritium salted out in the form of tritiated water ($H_2O$) during the reaction. The inhibition obtained for each concentration of each inhibitor product of the invention was calculated as a percentage of the controls (arbitrary 100%, obtained in absence of any inhibitor). The $IC_{50}$ equal to the concentration of inhibitor necessary to decrease by 50% the enzymatic activity. The $IC_{50}$ values obtained for the inhibitor products of the invention were as follows:

Product of Example 2: $IC_{50} = 1.8.10^{-7}$M.

Various modifications of the products and methods of the invention may be made without departing from the spirit or scope thereof and it is to be understood that the invention is intended to be limited only as defined in the appended claims.

What we claim is:

1. A compound of the formula wherein R is selected from the group consisting of alkyl, alkenyl and alkynyl of up to 4 carbon atoms, Y is =O or $R_1$ is hydrogen or acyl, n is 0, 1 or 2, D is =O and A and B form a second carbon-carbon bond or an α-epoxy.

2. A compound of claim 1 of the formula wherein R' is alkyl of 1 of 4 carbon atoms and A and B have the definition of claim 1.

3. A compound of claim 1 selected from the group consisting of 10β-[2-methylthio-ethyl]-Δ$^{4,9(11)}$-estradiene-6β-ol-3,17-dione and 9α, 11α-epoxy-10β-[2-methylthio-ethyl]-Δ$^{4,9}$-estrene-6β-ol-3,17-dione.

4. An aromatase inhibiting composition comprising an aromatase inhibiting effective amount of at least one compound of claim 1 and an inert pharmaceutical carrier.

5. A composition of claim 4 wherein the active compound is selected from the group consisting of 19β-[2-methylthio-ethyl ]-Δ$^{4,9}$(11)-estradiene-6β-ol-3,17 -dione and 9α,11α-epoxy-10β-[2-methylthio-ethyl]-Δ$^{4,9}$-estrene-6β-ol-3,17-dione.

6. A method of inhibiting aromatase activity in warm-blooded animals comprising administering to warm-blood animals an aromatiase inhibiting effective amount of at least one compound of claim 1.

7. The method of claim 6 wherein the compound is selected from the group consisting of 10β-[2-methylthio-ethyl]-Δ$^{4,9(11)}$-estradiene-6β-ol-3,17-dione and 9α, 11α-epoxy-10β-[2-methylthio-ethyl]-Δ$^{4,9}$-estrene-6β-ol-3,17-dione.

* * * * *